US011179430B2

(12) United States Patent
Walbroel et al.

(10) Patent No.: US 11,179,430 B2
(45) Date of Patent: Nov. 23, 2021

(54) EXTRACTS FROM MOTHER-OF-THYME AND THE USE THEREOF

(71) Applicant: Finzelberg GmbH & Co. KG, Andernach (DE)

(72) Inventors: Bernd Walbroel, Königswinter (DE); Ivo Pischel, Rossbach (DE); Björn Feistel, Andernach (DE)

(73) Assignee: Finzelberg GmbH & Co. KG, Andernach (DE)

( * ) Notice: Subject to any disclaimer, the term of this patent is extended or adjusted under 35 U.S.C. 154(b) by 0 days.

(21) Appl. No.: 14/405,114

(22) PCT Filed: Jun. 10, 2013

(86) PCT No.: PCT/EP2013/061917
§ 371 (c)(1),
(2) Date: Dec. 2, 2014

(87) PCT Pub. No.: WO2013/182709
PCT Pub. Date: Dec. 12, 2013

(65) Prior Publication Data
US 2015/0132414 A1    May 14, 2015

(30) Foreign Application Priority Data
Jun. 8, 2012 (EP) ..................... 12171273

(51) Int. Cl.
*A61K 36/53* (2006.01)
*A61K 47/26* (2006.01)

(52) U.S. Cl.
CPC .............. *A61K 36/53* (2013.01); *A61K 47/26* (2013.01); *A61K 2236/30* (2013.01)

(58) Field of Classification Search
None
See application file for complete search history.

(56) References Cited

U.S. PATENT DOCUMENTS

| | | | | |
|---|---|---|---|---|
| 2007/0184133 A1* | 8/2007 | Tripp | ..................... | A61K 31/12 424/745 |
| 2007/0218114 A1 | 9/2007 | Duggan et al. | | |
| 2011/0281956 A1* | 11/2011 | Park | ........................ | A61K 36/53 514/731 |

FOREIGN PATENT DOCUMENTS

| | | |
|---|---|---|
| DE | 42 13 167 A1 | 10/1993 |
| DE | 102008053034 A1 | 4/2010 |
| EP | 0 577 481 B1 | 6/1993 |
| EP | 1 080 727 A1 | 8/1999 |
| GN | 102046181 A | 5/2011 |
| JP | 2009 276245 A | 11/2009 |
| KR | 2003-0006163 A | 1/2003 |
| UA | 64 193 A | 2/2004 |
| UA | 93849 C2 | 3/2011 |
| WO | 2006 111624 A2 | 10/2006 |
| WO | 2010 023422 A1 | 3/2010 |

OTHER PUBLICATIONS

Stanojevic et al. (2013) Plant Foods Hum. Nutr. 68: 235-240.*
Kulisic et al. (2006) Food Technol. Biotechnol. 44 (4) 485-492.*
Pavel et al. (2011) Farmacia, vol. 59, 77-84.*
Ballabh et al. (2009) Indian Journal of Traditional Knowledge, vol. 8(2): pp. 185-190.*
Chun et al. (2001) Biol. Pharm. Bull. 24(8): 941-946.*
Pielesz (2012) Spectrochimica Acta Part A 93: 63-69.*
Raskin et al. (2004) Current Pharmaceutical Design, 10, 3419-3429.*
Revilla et al. (1998) J. Agric. Food Chem. 46, 4592-4597.*
Fachini-Queiroz et al. (2012) Evidenced-Based Complementary and Alternative Medicine, vol. 2012, Article ID 657026, 10 pages.*
Guerin-Deremaux (2010) Nutr. Res. Pract. 4(6): 470-476.*
Pavel et al. (2011) Farmacia, vol. 59, 1: 77-84.*
Pouillart et al. (2010) Inflamm Bowel Dis. vol. 16, No. 5, 783-794.*
Silva et al. (2012) J. Med Food 15 (11): 984-991.*
Zaidi et al. (2009) J. Ethnopharmacology 121: 286-291.*
Fecka et al. (2008) Food Chemistry 108: 1039-1053. (Year: 2008).*
Kulisic et al. (2006) Food Technol. Biotechnol. 44(4): 485-492. (Year: 2006).*
Stanojevic et al. (2013) Plant Foods Hum Nutr. 68:235-240. (Year: 2013).*
Basant Ballabh and O. P. Chaurasia; Medicinal Plants of Cold Desert Ladakh Used In The Treatment Of Stomach Disorders; Indian Journal of Traditional Knowledge, vol. 8, (2), Apr. 1, 2009, pp. 185-190.
Burns R.C. et al.; Antibody Blockade of ICAM-1 and VCAM-1 Ameliorates Inflammation in the SAMP-1/Yit Adoptive Transfer Model of Crohn's Disease In Mice; Gastroenterology, 121, 2001, pp. 1428-1436.
Bercik et al.; Is Irritable Bowel Syndrome A Low-Grade Inflammatory Bowel Disease?; Gastroenterol Clin North Am. vol. 34, 2005, pp. 235-245.
Damaskos & Kolios; Probiotics and Prebiotics In Inflammatory Bowel Disease; Microflora 'on the scope' Board Journal Clinical Pharmacol / 65:4 / 2008, pp. 453-467.
Database WPI; Thomson Scientific, London GB; AN 2009-R61151, XP002682747.
Kanai T. et al.; Homeostatic (IL-7) and Effector (IL-17) Cytokines as Distinct, but Complementary Target for an optimal therapeutic sliategy in inflammatory bowel disease, Current Opinion in Gastroenterology, 25, 2009, pp. 306-313.
La et al.; Peripheral Corticotropin Releasing Hormone Mediates Post-Inflammatory Visceral Hypersensitivity In Rats; World J Gastroenterol. 14(5), Feb. 7, 2008, pp. 731-736.
Mearin F. et al.; Irritable Bowel Syndrome and Inflammatory Bowel Disease, Is there a connection? Gastroenterol Hepatol; 32, (5), 2009, pp. 364-372.
Ogawa A. et al.; Neutralization of Interleukin-17; Aggravates dextran sulfate sodium-induced colities in mice; Clinical Immunology 110, 2004 pp. 55-62.

(Continued)

*Primary Examiner* — Russell G Fiebig
(74) *Attorney, Agent, or Firm* — Christensen, Fonder, Dardi & Herbert PLLC; Diane E. Bennett; Peter S. Dardi

(57) ABSTRACT

Extracts from *Thymus serpyllum* L. for use in enteric inflammatory diseases.

7 Claims, No Drawings

(56) References Cited

OTHER PUBLICATIONS

9O'Mahony SM., et al.; The Effects of Gabapentin in Two Animal Models of Co-Morbid Anxiety and Visceral Hypersensitivity; European Journal of Pharmacology, 667, 2011, pp. 169-174.

Pavel et al.; Phytochemical and Pharmacological Research On Some Extracts Obtained From Serphylli Herba, Farmacia ; 59, 1, 2011, pp. 77-84.

Petrovic et al.; The Antinociceptive Effects of Anticonvulsants In A Mouse Visceral Pain Model; Anesth Analg. 106, 2008, pp. 1897-1903.

Quigley; Irritable Bowel Syndrome and Inflammatory Bowel Disease: Practical Gastroenterology, Nov. 2010, pp. 31-37.

Raal et al.; Content and Composition of the Essential Oil of *Thymus serpyllum* L. Growing Wild in Estonia; Medicine, Kaunas, 40 (8), 2004; pp. 795-800.

Reinecker et al.; Enhanced Secretion of Tumour Necrosis Factor-Alpha, IL-6 and IL-1β by Isolated Lamina Propria Mononuclear Cells From Patients With Ulcerative Colitis and Crohn's Disease; Clin Exp Immunol; 94: 1993, pp. 174-181.

Rijcken et al.; ICAM-1 and VCAM-1 Antisense Oligonucleotides Attenuate In Vivo Leukocyte Adherence And Inflammation In Rat Inflammatory Bowel Disease; Gut 51, 2002, pp. 529-535.

Saiki T.; Myeloperoxidase Concentrations in the Stool as a New Parameter of IInflammatory Bowel Disease, Kurume Medical Journal, 45, 1998, pp. 69-73.

Sido et al.; Impairment of Intestinal Glutathione Synthesis In Patients with Inflammatory Bowel Disease; Gut 42, 1998, pp. 485-492.

Singh, Baljit; Psyllium As Therapectic And Drug Delivery Agent; International Journal of Pharmaceutics 334 (2007), pp. 1-14.

Russian Office Action of PCT/EP2013/061917; dated Dec. 15, 2016, 4 pages.

Ukrainian Institute Of Intellectual Property Office Action dated Sep. 20, 2017 of Application No. a 201414168, Nine pages.

Pouillart et al.; Nutriose, A Prebiotic Low-Digestible Carbohydrate, Stimulates Gut Mucosal Immunity And Prevents TNBS-Induced Colitis In Piglets, 12 pages (2009).

Akhmedov, "Plants: Your Friends And Enemies", Chapter 293. Mother-of-Thyme, UFA, 2007, 6 pages.

Huang et al.; "Herb Of Mother-Of-Thyme", China Medical Science and Technology Press, p. 126 (Aug. 31, 1998).

Chinese Office Action of Application No. 2013800302861, dated Sep. 25, 2017, 8 pages.

Office Action from corresponding Canadian Patent Application No. 2875908, PCT No. EP2013061917, dated Jun. 16, 2020.

\* cited by examiner

EXTRACTS FROM MOTHER-OF-THYME AND THE USE THEREOF

CROSS REFERENCE TO RELATED APPLICATIONS

This application is a national stage filing of PCT Application No. PCT/EP2013/061917 filed on Jun. 10, 2013, which claims priority to EP 12171273.1 filed on Jun. 8, 2012, both of which are incorporated herein by reference.

The present invention relates to extracts from wild thyme (*Thymus serpyllum*), the preparation thereof, and the use thereof.

A use of thyme (*Thymus* spp.) has been described, in particular, for culinary purposes, but also medically for diseases of the respiratory tract.

Thyme is a culinary plant and medicinal herb from the genus *Thymus*. Thyme is known for its strong taste and is cultured because of its thymol content, which is best done in hot and sunny habitats with highly permeable soils. Planted in spring, it grows as a perennial and can be propagated through seeds, cuttings or by root division. It is also often collected as a wild herb.

Thyme is found worldwide and is being used in the cuisines of Europe, the Middle East, Asia, India, Africa and America. In particular, thyme is employed for seasoning meat, soups and stews, as a single spice or in mixed herbs and spices. Thyme is contained as an important ingredient as Za'atar spice (Arabic for thyme) in meals of the Levantine countries, and it is a component of bouquet garni and of herbs of Provence.

Thyme is traded both in the fresh and dried state. The fresh product is available nearly all year from greenhouses, and it is very aromatic, but after the harvest, it will not keep longer than a week. Fresh thyme is sold in bunches of twigs, consisting of a woody stem bearing leaves and inflorescences. According to recipe, either whole twigs or the leaves without the twig are used. Dried thyme maintains its flavor better than many other herbs do.

In addition to culinary use, the essential oil providing the flavor has various medicinal functions. Thus, the thyme oil of common thyme (*Thymus vulgaris*) contains 20-54% thymol, which, being an antiseptic, is the main active ingredient, for example, in various mouthwashes, such as Listerine. In former times, the oil of thyme was also employed in wound healing in dressings, or topically against various fungi, and as an antibiotically active disinfectant. In contrast, the essential oil of wild thyme (*Thymus serpyllum*) has a high content of carvacrol, a terpene phenol that is stereoisomeric with thymol and has an analogous range of activity.

Aqueous infusions of thyme herb are employed for cough and bronchitis. Other medicinal applications include infections of the respiratory tract, in which thyme is applied in the form of tinctures, ointment, syrups or vapor inhalations, in addition to herbal tea. Since thyme has an antiseptic effect, a decoction or infusion in water can be employed very well against sore throats after cooling, if it is used for gargling several times a day. The absorbed thymol together with other volatile components of thyme herb is excreted through the lung (exhaled), and therefore, causes a reduction of the viscosity of the bronchial mucus because of its lipophilicity, whereby the latter can be coughed out more easily. In addition, they exert their antimicrobial effect in the respiratory tract. Other infections and wounds may also be treated with thyme decoctions.

Almost all the above properties and uses can be described for the regionally used thyme species. These vegetable drug delivering species include mainly *Thymus capitatus*, *Thymus citriodorus*, *Thymus mastichina*, *Thymus pulegioides*, *Thymus serpyllum*, *Thymus vulgaris*, and *Thymus zygis*. Traditionally, *T. zygis* is considered equivalent to *T. vulgaris*, but its economic importance is small. In this group, mainly *T. vulgaris* and *T. serpyllum* are available in economically significant amounts from culture or wild collection. In the European Pharmacopoeia, wild thyme (*Thymus serpyllum* L.) is stated as an undesirable adulteration of the medicinally employed thyme (*Thymus vulgaris* L.+*Thymus zygis*) (monograph 865), and vice versa. This due to the long known pharmacological difference between the plant species. The minimum content of essential oil in the monographed vegetable drugs is at least 3 ml/kg for wild thyme, and at least 12 ml/kg for common thyme.

In this grade, the pharmacologically valuable essential oil listed in the Ph. Eur. under the monograph 1374 is recovered exclusively from *T. vulgaris* or *T. zygis*.

Consequently, *T. serpyllum* and *T. vulgaris* are mostly treated separately in the specialized literature, and their activity is mainly attributed to the content of essential oils. In addition to the culinary use as mentioned above, there are also mentioned cosmetic perfume applications and, in particular, the treatment of diseases of the respiratory tract and cough, but also the popular applications with no clinical proof, such as externally for skin diseases and alterations, such as wounds, abscesses and burns, as well as internally as an antiseptic for inflammatory diseases of the urinary tract and the intestine etc. (HagerROM 2010).

In addition to these clinically unsubstantiated applications of thyme preparations relating to gastrointestinal complaints, there is a European Patent application EP 1 080 727 (A1), "Use of the extract of *Thymus vulgaris* for the preparation of a medicament for the treatment of Ulcerative Colitis and Crohn's disease" by Anastasios Emmanouilidis, claiming *Thymus vulgaris* and its ingredients, especially the essential oils, in combination with standard medicaments for these diseases, which is based on clinical case studies.

Also, the patent application DE4213167 (A1), "Medicament against gastritis, stomach and duodenal ulcers, and dyspepsia", by Suekrettin Guelduetuna describes the successful use of thyme oil. As to the mode of action, reference is made to the essential oil components thymol/carvacrol/cymene and cineole, and their activity against *Helicobacter pylori*.

In the patent specification EP 0 577 481 (B1), "New therapeutic application of a Thyme extract and in-vitro methods for inhibiting the growth and urease activity of *Helicobacter pylori*" by Itzhak Neeman, the antibacterial activity of aqueous extracts from *Thymus vulgaris*, *Thymus citriodorus* and *Coridothymus capitatus* is already described.

It is the object of the present invention to provide effective formulations of thyme, and to indicate further possible uses thereof.

This object is achieved by novel extracts and novel uses of these extracts.

Within the scope of systematic research activities, new applications of selected thyme species were surprisingly found. Thus, according to the invention, especially as described according to the present process, effective thyme preparations can be obtained, which are employed for inflammations, for example, chronic inflammatory diseases of the digestive tract, and irritable bowel syndrome.

Therefore, the invention relates to the use of extracts from *Thymus serpyllum* L. for treating inflammatory diseases, especially of the digestive tract.

The digestive tract includes the oral cavity, the pharynx, the esophagus, and the gastrointestinal tract.

In one embodiment, said inflammatory disease is an irritable bowel syndrome (IBS) or an inflammatory bowel disease (IBD).

In another embodiment, the inflammatory diseases are selected from the group of gingivitis, parodontitis, pharyngitis, esophagitis, gastritis, lymphocytic colitis, ulcerative colitis, diverticulitis, duodenitis, and Crohn's disease.

The invention further relates to an extraction process by which particularly effective extracts can be obtained, comprising the following steps:

a. providing a vegetable drug from aerial plant parts of *Thymus serpyllum* L.;
b. optionally drying said vegetable drug;
c. optionally comminuting said vegetable drug;
d. optionally destemming the leaves and reducing the stem content to less than 2% by weight;
e. optionally steaming the vegetable drug and reducing the essential oil to less than 0.5 ml/kg, based on the dried vegetable drug;
f. extracting the vegetable drug with an extractant;
g. at least partially removing the extractant to obtain a thick extract;
h. optionally defatting with liquid solvents;
i. optionally performing a thermal disinfection;
j. optionally adding a drying aid;
k. drying to obtain an extract.

Preferably, at least one of steps e, h or i is performed.

Surprisingly, it has been found that the extracts prepared according to the invention can be efficiently employed against inflammatory diseases, even if the components of the essential oil are substantially removed during the preparation of the extract. This can preferably be done either by steaming the vegetable drug prior to extraction, or by defatting by means of organic solvents, or by thermal disinfection.

In particular, suitable extractants are selected from the group of water, alcohol, ketone, ester, ether or supercritical gases, or mixtures thereof.

Preferably, water or a mixture of water and alcohol is employed as extractant. In the case of aqueous extractants, the alcohol contents are preferably within a range of from 0% by weight to 70% by weight, more preferably from 0% by weight to 40% by weight, or from 5% by weight to 40% by weight. Ethanol, in particular, but also methanol, n-propanol or isopropanol are particularly suitable as said alcohols. The use of $CO_2$ as an extractant is also preferred.

Extractions at a temperature of 20° C. to 100° C., preferably 50° C. to 90° C., more preferably 60° C. to 80° C., are particularly suitable, but are dependent on the selected extractant.

The employed vegetable drug preferably corresponds to the monograph "Serpylli herba" in the European Pharmacopoeia.

Drying is preferably performed by spray-drying or vacuum drying.

The invention also relates to an extract of aerial plant parts of *Thymus serpyllum* L. and, in particular, the extract obtainable by the above described process, or a corresponding extract formulation.

The invention also relates to a pharmaceutical formulation, medicinal product or food product, containing an extract from *Thymus serpyllum* L.

Preferably, this extract or extract formulation has a content of essential oil of at most 0.5% by weight, based on the dried extract, preferably at most 0.1% by weight, more preferably at most 0.01% by weight. The content of essential oils in the extract formulation is determined according to the method of the European Pharmacopoeia (Ph. Eur. 2.8.12) by analogy with the method for determining essential oil in vegetable drugs.

In accordance with the high tolerability of the previously known thyme preparations, it was the object of the present invention to provide a novel extract that is suitable for use in the entire range of inflammatory diseases. Local anti-inflammatory effects may be helpful along the entire digestive tract, as the case may be, in the treatment or prevention of inflammatory diseases. Gingivitis, parodontitis, pharyngitis, esophagitis and gastritis describe the inflammatory diseases of the upper part of the digestive tract. Lymphocytic colitis, ulcerative colitis, diverticulitis, duodenitis and Crohn's disease are, in addition to IBD and IBS, the best known representatives of inflammatory diseases of the intestinal region. Diseases of the intestinal region are the diseases belonging to the intestinal tract.

Because of the high volatility of the essential oil components, other groups of substances are also employed for analytical examinations of thyme preparations. Among these, the tannin rosmarinic acid, which is ubiquitous in the Lamiaceae family, is to be mentioned as the most prominent representative. Preferably, the preparations should have a content of at least 0.5% by weight rosmarinic acid for the analytical comparison of extract qualities to be as simple as possible. Of course, more is more readily detectable, which is why a minimum limiting concentration of 1.5% by weight rosmarinic acid, based on the dried native extract, appears to be realizable.

Therefore, extracts containing at least 0.5% by weight of rosmarinic acid, preferably at least 1% by weight of rosmarinic acid and more preferably 1.5% by weight of rosmarinic acid are particularly preferred.

In a preferred embodiment of the invention, the content of thymol plus carvacrol is <0.01% by weight, based on the dried native extract. All values relate to the native dried extract, i.e., the extract without the addition of auxiliary agents.

In one embodiment, the extract according to the invention is provided and used together with a prebiotic.

Among the further active components in chronic inflammatory diseases of the digestive tract and irritable bowel syndrome, prebiotic substances are often mentioned.

Prebiotic substances are human-indigestible food components that promote health by enhancing the growth and activity of bacteria in the digestive system.

They are functional food and as such, were described by Marcel Roberfroid in 1995. Typically, prebiotics are carbohydrates (such as oligosaccharides) rated as water-soluble dietary fibers, mostly belonging to the group of fructooligosaccharides (e.g., oligofructose and inulins).

Prebiotics are distinguished according to their chain length from short chain with 2-8 sugar building blocks, to long chain, such as inulin, with 9-64 saccharide units. Depending on molecular size, they are fermented as substrates faster or slower by different bacterial species in different segments of the intestine.

It is generally recognized that prebiotics improve the intestinal health of animals and humans as host organisms by increasing the number and activity of bifidobacteria and lactic acid bacteria. The positive effects of the bifidobacteria and lactic acid bacteria (lactobacilli) on the intestine of the host mainly include the improvement of digestion including an improved absorption of nutrients and minerals, and the effectiveness and intrinsic strengthening of the immune system. Bifidobacteria-stimulating products are referred to as bifidogenic factors.

Typical food sources providing prebiotics include carbohydrate-storing plants, such as soybeans and many cereals, and for example, Jerusalem artichokes and chicory roots are inulin-rich sources.

As to the ideal daily amount of prebiotics, there are different recommendations. They are typically within a range of from 4 to 8 g for supporting the general health of the digestive system. Up to 15 g or more is recommendable for severe digestive disorders.

Because of their advantages for health, prebiotic oligosaccharides are increasingly added to foods. These include, in particular, fructooligosaccharides (FOS), xylooligosaccharides (XOS), polydextrose and galactooligosaccharides (GOS). Mannooligosaccharides are often used in pet food for such prebiotic purposes.

In the patent specification WO 2010/023422 (A1), "Use of prebiotic Galacto-Oligo-saccharides in the treatment of intestinal inflammation" by Tzortzis et al., in vivo data in a DSS mouse model relating to prebiotics are already presented. Also in WO 2006/111624 (A1), "Anti-inflammatory and/or analgesic composition for the intestine comprising branched maltodextrine" by Wils et al., fructooligosaccharides are successfully examined for their anti-inflammatory effect in a mouse model. They are today available on the commodity market under the designations of ACTILIGHT, FIBERSOL, NUTRIOSE or RAFTILOSE.

Many of these prebiotics occur as natural plant carbohydrates, some are technically modified to adapt their properties for dietetic purposes. Thus, for example, cereal starches are converted to more or less digestion-resistant homoglucans or dextrins by processes of food technology, such as heating, acid or enzymatic treatment, and these can be employed very well as prebiotic dietary fiber. More recently, genetic engineering methods for producing inulins have also become established.

Preclinical and clinical studies show positive effects on mineral absorption, especially of calcium, hypertension (increased blood pressure), chronic inflammatory bowel diseases (Crohn's disease and ulcerative colitis), reduction of the risk of colon cancer, general promotion of the digestion, and intestinal regulation of the intestinal pH, and a potent effectiveness on the immune system and its stimulation.

These versatile effects on health are explained in terms of the increased production of short-chain fatty acids (SCFA) from the prebiotic oligosaccharides by the stimulated beneficial intestinal bacteria.

Because the uptake of large amounts of prebiotics with the food may temporarily lead to an increase of gases, flatulence or bowel movements, the ingestion of prebiotic-containing food should accordingly be increased slowly in order that a healthy bacterial flora can establish step by step.

The prebiotics employed are preferably selected from the group of dietary fibers, especially the group of carbohydrates, more preferably the group of water-soluble carbohydrates. Preferably, these may be employed as drying auxiliaries, thus supporting the drying and effectiveness. The use of ACTILIGHT®, FIBERSOL®, NUTRIOSE® or RAFTILOSE® is particularly preferred.

In medicine, chronic inflammatory bowel diseases (IBD) are defined as a group of inflammatory diseases of the large and small intestines. The most important main forms of IBD are Crohn's disease and ulcerative colitis (UC).

Much rarer types, which are also to be included in the chronic inflammatory bowel diseases, are collagenous colitis, lymphatic colitis, ischemic colitis, diversion colitis, Behçet's disease, and non-classifiable colitis.

Crohn's disease and ulcerative colitis are mainly distinguished by the location and nature of the inflammatory alterations. Crohn's disease may affect any part of the gastrointestinal tract, from the mouth to the anus, but mostly starting in the terminal ileum. In contrast, ulcerative colitis is limited to the large intestine and rectum.

In histological terms, ulcerative colitis is limited to the mucosa (intestinal epithelium), whereas Crohn's disease affects the entire intestinal wall as a consequence of transmural lesions.

Crohn's disease and ulcerative colitis are often associated with non-intestinal symptoms, such as liver diseases, arthritis, skin phenomena, and eye problems. Also, in the beginning, a clear diagnosis of Crohn's disease or ulcerative colitis is difficult to make, so that it is said to be a non-classifiable colitis.

In addition, these diseases occur with the following very different symptoms: abdominal pain, vomiting, diarrhea, rectal bleeding, severe interior cramps and muscular spasms in the pelvic region, loss of weight and the various associated complaints or diseases mentioned above, such as arthritis, pyoderma gangrenosum, and primary sclerosing cholangitis. The final diagnosis is usually made by a coloscopy with biopsy of the pathologically altered bowel regions.

The optimum therapy of chronic inflammatory bowel diseases generally depends on the existing disease type of IBD. However, for example, mesalazine (5-ASA) or the corresponding prodrug sulfasalazine are administered in both ulcerative colitis and Crohn's disease. Basically, immunosuppressants, such as prednisone, TNF inhibitors, and the cytostatics azathioprine, methotrexate or 6-mercaptopurine are employed, depending on the severity of the IBD symptoms. In severe cases, surgery may be required, such as partial intestinal resection, strictureplasty, or temporary or permanent colostomy or ileostomy.

As a rule, the treatment is started by administering medicaments with a strong anti-inflammatory effect, such as prednisone. As soon as the anti-inflammatory effect has been successful, the patient is treated with a milder medicament, such as mesalazine, in order to achieve remission of the disease. If this is not successful, a combination of the above mentioned immunosuppressants with mesalazine, which also displays an anti-inflammatory action, can be administered.

Although IBD strongly limits life quality because of pain, vomiting, diarrhea and other socially inacceptable symptoms, the disease alone rarely has a deadly outcome. Deaths because of complications, such as toxic megacolon, intestinal perforation and surgical complications, are also rare. Although IBD patients are at an increased risk of colon cancer, such a cancer is discovered by coloscopy and treated very much earlier than it would be in the general population, because of a routine monitoring of the large intestine.

The objective of the treatment after remission has been reached is to use milder medicaments having less potential side effects. Between these remission phases, which may last for months or years, flare-ups, i.e., acute relapses of the original symptoms, may occur at any time and mostly may prevail for several weeks.

For some time, novel therapeutic strategies have been reported that seem to be promising in many forms of chronic inflammatory bowel diseases.

First reports suggest that a "helminthic therapy", in which intestinal parasites, such as *Trichuris suis* or the hookworm *Necator americanus*, are administered, has very positive effects on the IBD symptom, and it is speculated that, in addition to a stimulation of the immune system, a persistent "immunization" effect may be responsible for the healing effect.

It is hoped that the use of prebiotics and probiotics, in particular, will lead to effective treatments of IBD, and in some studies, they have proven equally effective as prescription medicines.

An equally positive impact on IBD symptoms is attributed to cannabis preparations. The cannabis plant contains more than 50 so-called plant-specific cannabinoids, of which Δ9-tetrahydrocannabinol (THC) and cannabidiol (CBD) seem to be the best known and most active ones. Cannabinoids have a strong anti-inflammatory effect, especially through the CB2 receptor. This could also be detected in preclinical studies in rodents. Furthermore, it has been observed that the cell-mediated immunity is impaired in chronic cannabis users. The study of the functional role of the endocannabinoid system in immunomodulation shows that it is involved in almost all immunological activities. Cannabinoids move the balance of pro-inflammatory cytokines and anti-inflammatory cytokines towards type 2 profile T helper cells (Th2 phenotype) and suppress cell-mediated immunity, whereas humoral immunity is enhanced.

Irritable bowel syndrome (IBS) is a disorder of the entire digestive tract, causing abdominal pain and bloating as well as constipation or diarrhea, a variety of substances and emotional factors being able to trigger symptoms of IBS. Usually a doctor will diagnose IBS on the basis of the symptoms after having excluded other intestinal problems, for example, by blood and stool tests, and sigmoidoscopy for differential diagnosis to IBD (Crohn's disease, ulcerative colitis), cancer or other chronified bowel inflammations.

Symptoms include abdominal pain associated with bowel movement (defecation), which usually improves thereafter. Change in stool frequency (such as constipation or diarrhea) or consistency, abdominal expansion, mucus in the stool, and the feeling of incomplete emptying after defecation are further problems.

A healthy and regular diet is paramount in irritable bowel syndrome, and additional medications can relieve specific symptoms.

IBS affects about 10 to 20% of the general population in industrialized countries (e.g., up to 50% in Mexico), females with IBS being more likely to seek medical advice. In Germany alone, 7 million sufferers are believed to exist. Thus, IBS is the most common disease diagnosed by gastroenterologists. IBS belongs to functional gastrointestinal disorders, together with irritable stomach (functional dyspepsia).

The cause of irritable bowel syndrome is not understood. In many people with IBS, the digestive tract is particularly sensitive to many stimuli. Here, disturbances in the abdominal neuroplexus or its communication with the CNS are assumed. Furthermore, emotional factors (e.g., stress, depression and anxiety) as well as diet, medications, hormonal fluctuations or even minor irritations play a major role and can trigger or worsen IBS symptoms.

Since most people with IBS appear physically healthy, a psychosomatic cause of IBS was rather considered in the past, but recently, "mini-inflammations" were discovered at the Technical University of Munich (TUM), and related neuronal communication disorders in the nervous complex of the intestine were discussed as a cause. These inflammatory foci bring IBS in closer connection with IBD, which may also offer an anti-inflammatory treatment of irritable bowel similar to IBD (1. Bercik P, Verdu E F, Collins S M. Is irritable bowel syndrome a low-grade inflammatory bowel disease? Gastroenterol Clin North Am. (2005) Vol. 34, Issue: 2: 235-45//2. Mearin F, Perelló A, Balboa A; Irritable bowel syndrome and inflammatory bowel disease: Is there a connection? Gastroenterologia y hepatologia (2009) Volume: 32, Issue: 5, Pages: 364-372//3. Quigley E M M, Shanahan F; Irritable Bowel Syndrome and Inflammatory Bowel Disease: Is There an Overlap? Practical Gastroenterology, November 2010, 31-37).

The treatment is person-specific and at first consists in the avoidance or elimination of the cause, for example, if certain foods or stress types trigger the problem. If constipation additionally occurs, regular physical activity is often helpful to restore normal digestion. Basically, an IBS can be positively affected relatively well by a corresponding change in diet, or keeping to a diet.

If constipations prevail, it often helps to supply more roughage and fiber materials or other digestion-promoting agents, such as bran, Indian psyllium (Metamucil), methylcellulose, sorbitols, lactulose, constulose, polyethylene glycols, glycerol and bisacodyl (Dulcolax) or lubiprostone (Amitiza). In addition, a direct efficacy in IBD and IBS has also been postulated for psyllium (Baljit Singh: Review— Psyllium as therapeutic and drug delivery agent; International Journal of Pharmaceutics 334 (2007) 1-14).

Relaxants for the smooth muscles of the intestine, such as dicyclomine (Bentyl) or butylscopolamine (Buscopan), can relieve the abdominal pain and cramps. In contrast, if diarrheas prevail, antidiarrheals, such as the opiate analogue loperamide (IMODIUM) or the herbal UZARA, an extract from *Xysmalobium undulatum*, should be employed. For diarrheas associated with nausea, alosetrone (U.S. trade name: Lotronex), a selective inhibitor of 5-HT3 receptors, may be employed. Comparable antiserotonergic effects have recently been attributed to ginger.

Antidepressants as well as techniques for behavior modification (such as cognitive behavioral therapy), psychotherapy and hypnosis are also employed for the treatment of IBS symptoms, often showing a good efficacy. Even a long-term use of antidepressants is relatively safe, and antidepressants cannot only reduce pain and other symptoms, but also relieve insomnia, depression or anxiety.

In addition to these therapies with chemical pharmaceuticals, phytotherapeutic preparations are increasingly employed, especially aromatic oils, such as peppermint oil, which are very effective in IBS symptoms, such as bloating and abdominal cramps.

Furthermore, probiotics and prebiotics have become an important therapeutic component in IBS as well as IBD (Damaskos & Kolios: Probiotics and prebiotics in inflammatory bowel disease: microflora 'on the scope' 2008 Br J Clin Pharmacol/65:4/453-467). In addition, many plant extracts containing so-called "soluble fibers", such as a fiber-rich cladodes extract from *Opuntia ficus* indica L., also belong to prebiotics. These water-soluble carbohydrates relieve the gastrointestinal tract, e.g., by emulsifying lipids and thereby releasing them with delay, but also by the fact that these carbohydrates themselves are metabolized only by some desired bacterial species in the intestinal flora, thus contributing to a shift in the proportional abundance of individual species of bacteria.

The invention is further illustrated by the following non-limiting Examples.

EXAMPLES

Methods

Determination of Rosmarinic Acid

The quantitative determination of rosmarinic acid is effected by means of gradient HPLC on an RP18 phase (preferably LiChrospher 100, RP 18, 5 µm, 250×4 mm), with detection at 320 nm. The binary eluent consists of A (15% by volume acetonitrile+0.425% phosphoric acid+84.575% water) and B (80% by volume acetonitrile+0.425% phosphoric acid+19.575% water) and is run in a ramp profile with 1 ml/min from 100% A to 30% A+70% B within 40 minutes. The injection volume is 10 µl.

As a reference, 25 mg of rosmarinic acid is accurately weighed and dissolved in 100 ml of methanol; 10 ml thereof is diluted to 100 ml.

For the test solution, 400 mg of thyme extract is dissolved in a 100 ml volumetric flask containing 25 ml of water and 25 ml of methanol in an ultrasonic bath. After thermal equilibration at RT, the volumetric flask is filled to the mark with 50% methanol, and mixed thoroughly. 10 ml of the solution is diluted to 100 ml with 50% methanol.

Determination of Thymol and Carvacrol

The quantitative determination of the essential oil substances thymol and carvacrol is effected by means of gas chromatography. Thus, a fused silica capillary column (e.g., from Zberon ZB-FFAP, code 7JM-G009-17) with 50 m length and an internal diameter of 0.32 mm is used. Hydrogen 5.0 with a flow rate of 2.5 ml/min is used as the carrier gas. An FID detector (250° C.) is suitable for detection. The GC working conditions are: 140° C. (1 min isothermal), heating from 140° C. to 190° C. with 5° C./min, then 190° C. (5 min isothermal), further heating from 190° C. to 220° C. with 20° C./min, then 220° C. (9 min isothermal).

As reference substances, pure thymol (Merck 108167) and carvacrol (Fluka 22051), 50.0 mg each, are added to a 50 ml volumetric flask along with an internal standard substance (50.0 mg of 4-isopropylphenol), and filled with n-hexane up to the mark.

A separate solution of 250.0 mg of 4-isopropylphenol as internal standard substance is dissolved in and filled up with n-hexane in a 250 ml volumetric flask.

Thyme extracts of approximately 1 g are weighed and dissolved in 40 ml of 30% v/v methanol. After transfer to a 250 ml separatory funnel, 5 ml of the internal standard solution is added. The entire solution is partitioned three times with 40 ml diethyl ether. The combined diethyl ether phases are dried over sodium sulfate, filtered clear and concentrated by evaporation on a rotary evaporator at 40° C. under partial vacuum. The residue is taken up in 5.0 ml of 96% ethanol. Of this solution, 1 µl is injected (temperature of the injector: 230° C.).

The GC chromatogram contains carvacrol as a dominant peak (about 12.7 min at RT) for wild thyme extracts, whereas thymol has a peak area that is smaller by about one third (about 12.1 min at RT). The internal standard 4-isopropylphenol is near this peak group with about 12.9 min at RT.

Example 1

Thyme Aqueous Extract (Prior Art)

14.3 kg of destemmed and dried vegetable drug of Herba Thymi Ph. Eur. (thyme herb) (*Thymus vulgaris*) is steamed with overheated steam at 134° C. in a Holstein-Kappert percolator for 1.5 hours, until the smell of essential oil components can no longer be noted in the exhaust air (<0.5 ml/kg of drug). Subsequently, extraction is effected in the percolator with 286 liters of osmosis water at 60° C. The eluate is drained over the drug and freed from drug residues through a sieve bag with 250 µm pore size. By a plate evaporator, the eluate is concentrated to a thick extract with about 53% proportion of dry substance. Of the viscous extract obtained, 70% dry extract equivalent is admixed with 30% maltodextrin Ph. Eur., autoclaved at 121° C. for 15 minutes, and dried at 50° C. in a vacuum drying cabinet. The extract obtained is characterized by a $DEV_{native}$ of 4:1 (DEV=drug-to-extract ratio), a content of essential oil of <0.1%, of which thymol/carvacrol <0.01%, and a content of rosmarinic acid of 2.5%.

Example 2

Wild Thyme Aqueous Extract 17.8 kg of destemmed and dried vegetable drug of Herba Serpylli Ph. Eur. (*Thymus serpyllum*) is steamed with overheated steam at 134° C. in a Holstein-Kappert percolator for 1.5 hours, until the smell of essential oil components can no longer be noted in the exhaust air. Subsequently, extraction is effected in the percolator with 356 liters of osmosis water at 60° C. The eluate is drained over the drug and freed from drug residues through a sieve bag with 250 µm pore size. By a plate evaporator, the eluate is concentrated to a thick extract with about 50% proportion of dry substance.

Example 3

Wild Thyme Aqueous Extract 1

The viscous extract obtained according to Example 2 is dried in a native state at 50° C. in a vacuum drying cabinet. The extract obtained is characterized by a $DEV_{native}$ of 6:1, a content of essential oil of <0.1%, of which thymol/carvacrol <0.01%, and a content of rosmarinic acid of 2.6%.

Example 4

Wild Thyme Aqueous Extract 2

Of the viscous extract obtained according to Example 2, 70% dry extract equivalent is admixed with 30% Nutriose FB 06, autoclaved at 121° C. for 15 minutes, and dried at 50° C. in a vacuum drying cabinet. The extract obtained is characterized by a $DEV_{native}$ of 6:1, a content of essential oil of <0.1%, of which thymol/carvacrol <0.01%, and a content of rosmarinic acid of 1.8%.

Example 5

Wild Thyme 20% Ethanol Extract 500 g of destemmed and dried vegetable drug of Herba Serpylli Ph. Eur. (*Thymus serpyllum*) is extracted twice with 5 liters each of 20% (v/v) ethanol at 50° C. in a percolator. The eluate is drained over the drug and freed from drug residues through a star-pleated filter (32-WE). In a rotary evaporator, the eluate is concentrated to a thick extract with about 50% proportion of dry substance under a low vacuum of <50 mbar. The thus obtained viscous extract is admixed with 30% Nutriose FB 06, autoclaved at 121° C. for 15 minutes, and dried at 50° C. in a vacuum drying cabinet. The extract obtained is characterized by a $DEV_{native}$ of 6:1, a content of essential oil of <0.1%.

Example 6

Wild Thyme 40% Ethanol Extract 500 g of destemmed and dried vegetable drug of Herba Serpylli Ph. Eur. (*Thymus serpyllum*) is extracted twice with 5 liters each of 40% (v/v) ethanol at 50° C. in a percolator. The eluate is drained over the drug and freed from drug residues through a star-pleated filter (32-WE). In a rotary evaporator, the eluate is concentrated to a thick extract with about 50% proportion of dry substance under a low vacuum of <50 mbar. The thus obtained viscous extract is admixed with 30% Nutriose FB 06, autoclaved at 121° C. for 15 minutes, and dried at 50° C. in a vacuum drying cabinet. The extract obtained is characterized by a $DEV_{native}$ of 6:1, a content of essential oil of <0.1%.

Example 7

Wild Thyme 70% Ethanol Extract 500 g of destemmed and dried vegetable drug of Herba Serpylli Ph. Eur. (*Thymus serpyllum*) is extracted twice with 5 liters each of 70% (v/v) ethanol at 50° C. in a percolator. The eluate is drained over the drug and freed from drug residues through a star-pleated filter (32-WE). In a rotary evaporator, the eluate is concentrated to a thick extract with about 50% proportion of dry substance under a low vacuum of <50 mbar. The thus obtained viscous extract is admixed with 30% Nutriose FB 06, autoclaved at 121° C. for 15 minutes, and dried at 50° C. in a vacuum drying cabinet. The extract obtained is characterized by a $DEV_{native}$ of 6:1, a content of essential oil of <0.1%.

Example 8

Wild Thyme CO$_2$ Extract 500 g of destemmed vegetable drug of Herba Serpylli Ph. Eur. (*Thymus serpyllum*) is steamed with overheated steam and substantially freed from essential oil. The vegetable drug is dried and comminuted to powder form, transferred to a pressurized gas system, where it is extracted with 95% supercritical carbon dioxide and 5% ethanol (as modifier) at 200 bar and at 60° C. for 60 minutes. After release into the product discharge vessel, an extract resulted with an average $DEV_{native}$ of 18:1 and a flavonoid content of about 2.3%. The content of essential oil was only 0.45%, based on the dry native extract. The thus obtained extract was processed with 30% Fibersol to give a homogeneous extract, and ground in a Starmix.

Example 9

In Vitro Test Model

Lipopolysaccharide(LPS)-induced release of tumor necrosis factor alpha (TNFα) in peripheral human monocytes.

Human primary monocytes are recovered from the buffy coat of healthy human blood donors in a standardized procedure. The cells are sown in 24-well plates for the ELISA tests.

Monocytes are stimulated with 10 ng/ml LPS in a 24-well cell culture plate at 37° C. and 5% CO$_2$ for 24 hours. The extracts are added 30 min before the LPS addition in order to test whether they can prevent the LPS-inducing effects. After 24 hours, the cell supernatants are withdrawn, centrifuged and examined for TNFα concentrations in an ELISA according to the manufacturer's instructions (Biotrend, Germany; Immunotools, Germany).

TABLE 1

|  | TNFα release at 50 μg/ml |
|---|---|
| *Thymus vulgaris* aqueous (Example 1) | 85% |
| *Thymus serpylli* aqueous (Example 4) | 58% |
| *Thymus serpylli* 20% EtOH (Example 5) | 90% |
| *Thymus serpylli* 40% EtOH (Example 6) | 62% |
| *Thymus serpylli* 70% EtOH (Example 7) | 53% |

It is found both that an aqueous extract from *Thymus serpyllum* is clearly superior to an aqueous extract from *Thymus vulgaris*, and that, in addition to the purely aqueous extract, higher ethanolic extracts of 40% to 70% also show a comparably good inhibition.

The fact that TNF-alpha is related to the claimed diseases is supported by the literature (Reinecker et al.: Enhanced secretion of tumour necrosis factor-alpha, IL-6, and IL-1fi by isolated lamina propria mononuclear cells from patients with ulcerative colitis and Crohn's disease; Clin Exp Immunol 1993; 94: 174-181).

Example 10

In Vivo DSS Test Model

This study was performed in accordance with the Directive on the protection of animals used for experimental and other scientific purposes of the European Union (86/609/EEC).

The test system using DSS (=dextran sodium sulfate in mice to induce colitis is widely used and scientifically accepted.

In the present test series, 7-9 week old female mice (strain C57/BL6J) with an average body weight of 20 g are used; they are held in air-conditioned animal quarters with 12 hours light-dark cycle in Makrolon cages, fed standard rodent food and water ad libitum throughout the experiment.

The mice are randomly assigned to seven groups (n=8). Except for the healthy control group, all animals obtain a concentration of 3% DSS in the drinking water from day d(−4) to d(0) to induce colitis. Subsequently, the drinking water is returned to normal, and the curative approach of the test series may begin. Two groups (healthy and sick control groups) obtain only the administration medium orally, and the test groups obtain either 100 mg/kg BW or 250 mg/kg BW of a thyme extract formulation according to Example 1, or 100 mg/kg BW or 250 mg/kg BW of a wild thyme extract formulation according to Example 4, or 50 mg/kg BW of the chemical reference substance sulfasalazine (SAZ). The substances are respectively administered as a solution/suspension through a gastric tube for a period of 7 days. On d(7), the animals are sacrificed by an overdose of halothane, and the intestine is removed for evaluating the intestinal damage. A surrogate parameter that is closely related with the inflammatory gastrointestinal diseases is IL-17 (1. Takanori Kanai et al.: Homeostatic (IL-7) and effector (IL-17) cytokines as distinct but complementary target for an optimal therapeutic strategy in inflammatory bowel disease, Current Opinion in Gastroenterology 2009, 25: 306-313//2. Atsuhiro Ogawa et al.: Neutralization of interleukin-17 aggravates dextran sulfate sodium-induced colitis in mice, Clinical Immunology 110 (2004), 55-62), which was determined by RT-PCR and based on β-actin expression as an internal standard.

The intercellular adhesion molecule ICAM-1 was also determined by RT-PCR (1. R. C. Burns et al.; Antibody blockade of ICAM-1 and VCAM-1 ameliorates inflammation in the SAMP-1/Yit adoptive transfer model of Crohn's disease in mice; Gastroenterology Volume 121, Issue 6, Pages 1428-1436, December 2001//2. E. Rijcken et al.; ICAM-1 and VCAM-1 antisense oligonucleotides attenuate in vivo leukocyte adherence and inflammation in rat inflammatory bowel disease; Gut 2002; 51: 529-535).

100 mg/kg BW sulfasalazine (SAZ) in the reference group. All test substances are administered once a day as a solution or suspension through a gastric tube for a period of 7 days. The administration of the test substances starts at the same day as the colitis induction. For this purpose, the rats are fasted over night, and then a colitis is induced in both the sick control group and the treatment groups with TNBS as follows: During a halothane anesthesia, a solution (10 mg of TNBS dissolved in 0.25 ml of ethanol 50% v/v) is injected from a Teflon cannula through the anus 8 cm deep into the intestine. The rats of the healthy control group are administered 0.25 ml of a PBS solution instead of the TNBS solution. The body weight, the water and food intake and the stool consistency are recorded daily during the testing

TABLE 2

|  | Healthy control group | Colitic control group | Thymus serpylli 100 mg/ kg BW | Thymus serpylli 250 mg/ kg BW | Thymus vulgaris 100 mg/ kg BW | Thymus vulgaris 250 mg/ kg BW | Sulfasalazine 50 mg/ kg BW |
| --- | --- | --- | --- | --- | --- | --- | --- |
| IL-17 | 0.34 ± 0.04 | 0.69 ± 0.04 | 0.56* ± 0.04 | 0.50* ± 0.03 | 0.61 ± 0.02 | 0.75 ± 0.03 | 0.59* ± 0.04 |
| ICAM-1 | 0.27 ± 0.05 | 0.54 ± 0.04 | 0.41* ± 0.05 | 0.41* ± 0.03 | 0.57 ± 0.04 | 0.60 ± 0.05 | 0.37* ± 0.04 |

*$p < 0.05$ vs. control

It is to be seen that the excretion of both the IBD-related cytokine IL-17 and the integrin ICAM-1 is significantly reduced by the wild thyme extract according to the invention, whereas a *Thymus vulgaris* extract cannot confirm this effect.

Example 11

In Vivo TNBS Test Model

This study was performed in accordance with the Directive on the protection of animals used for experimental and other scientific purposes of the European Union (86/609/EEC).

Female Wistar rats (200-210 g) were kept in Makrolon cages in air-conditioned animal quarters with 12 hours light-dark cycle, fed standard rodent food and water ad libitum throughout the experiment. The rats are randomly assigned to six groups (n=10). Two groups (healthy and sick controls) obtain 1 ml of the administration medium orally, and the test groups obtain either 100 mg/kg BW of a wild thyme extract formulation according to Example 4, or 70 mg/kg BW of a wild thyme extract formulation according to Example 3, or 30 mg/kg BW of the prebiotic Nutriose, or period. One week after the start of the colitis induction, all the rats are sacrificed by an overdose of halothane, and the intestine is removed for evaluating the intestinal damage. The intestinal segment is cleaned from fat and mesenterium, and transferred to a filter paper. Each specimen is weighed, and its length is measured under a constant load (2 g), and the weight-to-length ratio is determined therefrom. Independently of the treatment employed, the intestine is evaluated macroscopically for visible damage on a scale of from 0 to 10 by two observers by means of previously defined criteria, which take the extension and severity of the damage into account. A section of the adjacent tissue near the distal diseased region is immediately fixed with 4% formaldehyde, and embedded in paraffin for histological studies. Subsequently, this preparation is divided into different segments for biochemical determinations. One piece is frozen at −80° C. for determining myeloperoxidase (MPO), another piece is immersed in 5% trichloroacetic acid for determining glutathione (GSH), and another piece is immediately processed for measuring the cytokine levels of IL-6 and the expression of iNOS. Finally, the remaining segment is used for RNA extraction and the subsequent analysis of the expression of different markers by means of qPCR.

TABLE 3

|  | Macroscopic score | Microscopic score | MPO [mU/g] | GSH [nmol/g] | IL-6 [ng/g] |
| --- | --- | --- | --- | --- | --- |
| healthy control | 0±= | 0±= | 155.1 ± 74.8 | 1872.8 ± 149.3 | 180.5 ± 13.1 |
| colitic control | 7.8 ± 0.2 | 28.1 ± 2.5 | 8969.6 ± 1402.0 | 877.4 ± 107.6 | 281.8 ± 26.8 |
| *Thymus serpylli* extract according to Example 3 (70 mg/kg) | 7.3 ± 0.3 | 12.1* ± 2.2 | 4629.3* ± 705.5 | 1066.1 ± 152.2 | 253.2 ± 10.7 |
| Nutriose (30 mg/kg) | 7.6 ± 0.4 | 23.6 ± 3.6 | 8468.4 ± 1461.5 | 977.6 ± 116.4 | 246.5 ± 19.9 |
| *Thymus serpylli* extract according to Example 4 (100 mg/kg) extract + Nutriose | 6.6* ± 0.4 | 9.6* ± 3.9 | 4099.7* ± 995.9 | 1490.8* ± 176.2 | 207.5* ± 18.1 |

TABLE 3-continued

|  | Macroscopic score | Microscopic score | MPO [mU/g] | GSH [nmol/g] | IL-6 [ng/g] |
|---|---|---|---|---|---|
| Sulfasalazine (100 mg/kg) | 6.9* ± 0.4 | 13.5* ± 3.2 | 5591.5 ± 537.0 | 1297.4* ± 184.3 | 222.0 ± 16.1 |

* = $p < 0.05$ vs. colitic control

From this Table, it can be seen that Nutriose could not exert a significant influence on any of the parameters. In contrast, not only could the potential of the native extract be enhanced by the addition of Nutriose (microscopic evaluation, MPO activity), but the native extract itself has become significantly effective only by the combination with Nutriose, in the parameters of macroscopic evaluation as well as the GSH content and IL-6 secretion. Even the chemical reference preparation sulfasalazine could not show significant improvements in all parameters.

Myeloperoxidase is specifically associated with chronic inflammatory diseases (Tomohisa Saiki: Myeloperoxidase concentration in the stool as a new parameter of IBD; Kurume medical journal, 45, 69-73, 1998). Glutathione is also evaluated in the literature in connection with IBD (Sido et al.: Impairment of intestinal glutathione synthesis in patients with inflammatory bowel disease; Gut 1998 42: 485-492).

Also, interleukin 6 is already associated with Crohn's disease and ulcerative colitis in the literature (Reinecker et al.: Enhanced secretion of tumour necrosis factor-alpha, IL-6, and IL-1fi by isolated lamina propria mononuclear cells from patients with ulcerative colitis and Crohn's disease; Clin Exp Immunol 1993; 94: 174-181).

Example 12

Measurement of the Influence on the Irritable Bowel Syndrome (IBS) in an Animal Model This study was performed in accordance with the Directive on the protection of animals used for experimental and other scientific purposes of the European Union (86/609/EEC). Male Sprague Dawley rats (240-320 g; Supplier Janvier, St Berthevin Cedex) are held in Makrolon cages with 3-4 animals/cage in air-conditioned surroundings with 12 hours light-dark cycle, and fed with standard rodent food and water ad libitum throughout the experiment. The rats are randomly assigned to four groups (n=10). All test substances are administered once a day as a solution or suspension through an enteric tube.

Two groups (healthy and sick controls) obtain 1 ml of the administration medium orally, and the test groups obtain either 100 mg/kg BW of a wild thyme extract formulation according to Example 4, or 70 mg/kg BW of gabapentin as a positive control. Gabapentin has already been described for this purpose in the literature on mice (Stepanovic-Petrovic R M, et al. The antinociceptive effects of anticonvulsants in a mouse visceral pain model. Anesth Analg. 2008; 106: 1897-903) and rats (O'Mahony S M, Coelho A M, Fitzgerald P, Lee K, Winchester W, Dinan T G, Cryan J F. The effects of gabapentin in two animal models of co-morbid anxiety and visceral hypersensitivity. Eur J Pharmacol. 2011; 667: 169-74).

The rats were anesthetized with isofluorane, and a cannula was introduced through the anus about 6 cm deep into the large intestine. Subsequently, 1 ml of 4 mM deoxycholic acid (DCA) dissolved in Krebs solution at pH 7.4 was administered while the cannula is slowly withdrawn. The animals were left in a "head down" position in order to prevent DCA from flowing out. The rats were administered DCA once a day on three consecutive days. The first injection was counted as day 1. Mice in the control group obtained 1 ml of 0.9% saline instead of DCA.

The determination of colorectal distension (CRD) was effected by the method of La et al. (La J H, Sung T S, Kim H J, Kim T W, Kang T M, Yang I S. Peripheral cortico-tropin releasing hormone mediates post-inflammatory visceral hypersensitivity in rats. World J Gastroenterol. 2008; 14: 731-6). The administration of the test substances started 24 hours after the last DCA administration and was performed through 1 week. Subsequently, the different groups were examined for visceral hypersensitivity towards colorectal distension. For this purpose, the rats were left without food over night (with free access to water) in order to facilitate balloon placement. On the day of the experiment, the rats were briefly anesthetized with isofluorane, and a balloon of 5-6 cm attached to a flexible tube was introduced through the anus into the rectum and descending colon, the distal end being 1 cm proximal to the external sphincter. The catheter is then glued to the base of the tail in order to prevent dislocation. After this procedure, the rats are placed in a transparent booth (20 cm×8 cm×8 cm), and allowed to recreate. After the animals are entirely awake and acclimatized, the CRD was produced by inflating the balloon with air. Each experiment consisted of five defined pulses (60 mm Hg) over a duration of 20 s with 3 min interval between the stimuli. Generally, 4 experiments were performed to reach a stable response (less than 20% variability between the last two experiments).

In this experiment, the abdominal withdrawal reflex (CRD) is rated as follows:

0=no behavioral response to distension,
1=brief head movements due to immobility,
2=contraction of abdominal muscles without lifting of abdomen,
3=lifting of abdomen,
4=body arching and lifting of pelvic structure.

From this score, the following results could be obtained after 1 week of treatment:

| | Animal group (n = 10) | | | |
|---|---|---|---|---|
| | Healthy group (no IBS) (A) | Sick group (IBS control) (B) | Extract of Example 4 (*T. serpylli*) (C) | Positive control (gabapentin) (D) |
| Mean value (standard deviation) | 0.25 (±0.125) | 2.875 (±0.25) | 0.375 (±0.06) | 0.06 (±0.03) |

The evaluation showed that rats treated with DCA (B=sick control group) exhibited a statistically significant difference to the untreated animals (A=healthy control group). Thus, the model was suitable in principle. The positive control gabapentin (D) could confirm the information from the literature and had a significant effect (p<0.05) as compared to the IBS control (B). The test substance (C), the inventive extract according to Example 4, could also confirm its suitability for the treatment of IBS. The *Thymus serpylli* extract was significantly lower than the IBS control group (B) (p<0.05), and was on the same level as the animals of the healthy group (A).

Example 13

Instant Extract Formulation

In order to extend the time to the next relapse as much as possible within the scope of a maintenance therapy, a dosage form that leads to a high compliance is needed. This can be well ensured, for example, by means of a quickly prepared instant beverage formulation. Thus, 50% dry extract equivalent of a viscous extract according to Example 3 is mixed with 43% Nutriose FB 06, 5% sucrose and 2% flavor, and dried in a spray tower by means of supercritical carbon dioxide to give an instant powder. This formulation can be filled in sachets and is readily soluble in cold water. The flavoring can be easily adapted to the market's needs.

Example 14

Extract Formulation as "Astronaut Food"

Unfortunately, patients suffering from Crohn's disease or ulcerative colitis are often in a poor state of health and only capable of ingesting a small amount of classical food. For those patients, an extract formulation is provided that is colloquially referred to as "astronaut food", but which is usually a high-calorie, nutraceutically balanced diet in the form of a 200 ml drinking formulation, or of a gel in a collapsible tube. To prepare such a gel, an extract formulation according to Example 4 is dissolved together with the other ingredients (vitamins, minerals, protein and free amino acids), homogenized, and portions of 80 ml each are filled into disposable collapsible tubes.

Thus, one collapsible tube (1 portion) contains:

1000 mg of wild thyme extract, 6 g of protein, 30 g of carbohydrates, of which 15 g of sugar (sucrose), 9 g of lipids, of which 1 g of saturated fatty acids, 44 g of water, minerals (96 mg of sodium, 91 mg of chloride, 236 mg of potassium, 174 mg of calcium, 174 mg of phosphorus (Ca/P ratio=1.0), 33 mg of magnesium), trace elements (3.8 mg of iron, 2.9 mg of zinc, 430 µg of copper, 32 µg of iodine, 16 µg of chromium, 200 µg of fluorine, 800 µg of manganese, 24 µg of molybdenum, 14 µg of selenium), vitamins (240 µg of vitamin A, 400 µg of vitamin B1, 400 µg of vitamin B2, 4.3 mg of niacin, 400 µg of vitamin B6, 64 µg of folic acid, 1300 µg of pantothenic acid, 700 µg of vitamin B12, 9.6 µg of biotin, 24 mg of vitamin C, 1.8 µg of vitamin D, 13 µg of vitamin K), 88 mg of choline.

The invention claimed is:

1. An ingestible formulation for treating inflammatory diseases of the intestinal tract comprising an effective amount of a dry composition comprising:
   an extract in an amount of 70% by dry weight, the extract prepared by reducing essential oils from aerial plant parts of *Thymus serpyllum* L. with steam to form steam treated plant parts, and then extracting the steam treated plant parts using water as an extractant to form the extract; and
   a prebiotic in an amount of 30% by weight, wherein said prebiotic is an exogenous water-soluble carbohydrate comprising dextrin,
   wherein the extract includes rosmarinic acid in an amount of at least 0.5% by dry weight and thymol plus carvacrol in an amount of <0.01% by dry weight.

2. The ingestible formulation of claim 1, wherein the prebiotic is a human-indigestible food component that promotes health by enhancing growth and activity of bacteria in a human digestive system.

3. The ingestible formulation of claim 1, wherein the extract includes essential oil in an amount of ≤0.5%.

4. The ingestible formulation of claim 1 having at least 4 grams of prebiotic.

5. The ingestible formulation of claim 1 wherein the ingestible formulation is in a drink or gel.

6. The ingestible formulation of claim 1 wherein the prebiotic comprises hydrolyzed starch comprising (1,2) or (1,3) non-digestible glycosidic bonds.

7. A method for treating inflammatory diseases of the intestinal tract, comprising administering a therapeutically effective amount of the ingestible formulation of claim 1 to a patient wherein the inflammatory disease is selected from the group consisting of irritable bowel syndrome (IBS), inflammatory bowel disease (IBD), lymphocytic colitis, ulcerative colitis, diverticulitis, duodenitis, and Crohn's disease.

* * * * *